United States Patent
Soma et al.

(10) Patent No.: US 10,391,137 B2
(45) Date of Patent: Aug. 27, 2019

(54) PLATELET-DERIVED GROWTH FACTOR-BB PRODUCTION PROMOTOR, AND MESENCHYMAL STEM CELL PRODUCTION ACCELERATOR, STEM CELL STABILIZER AND DERMAL REGENERATOR COMPRISING THE SAME

(75) Inventors: Tsutomu Soma, Yokohama (JP); Masato Iino, Yokohama (JP); Haruyo Yamanishi, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 1323 days.

(21) Appl. No.: 13/138,417

(22) PCT Filed: Jul. 1, 2011

(86) PCT No.: PCT/JP2011/065207
§ 371 (c)(1),
(2), (4) Date: Aug. 12, 2011

(87) PCT Pub. No.: WO2013/005281
PCT Pub. Date: Jan. 10, 2013

(65) Prior Publication Data
US 2013/0004533 A1    Jan. 3, 2013

(51) Int. Cl.
| | |
|---|---|
| A61K 36/539 | (2006.01) |
| A61K 36/899 | (2006.01) |
| A61K 36/064 | (2006.01) |
| A61K 36/38 | (2006.01) |
| A61K 36/45 | (2006.01) |
| A61K 31/05 | (2006.01) |
| A61K 31/661 | (2006.01) |
| A23L 33/105 | (2016.01) |

(52) U.S. Cl.
CPC .......... *A61K 36/539* (2013.01); *A23L 33/105* (2016.08); *A61K 31/05* (2013.01); *A61K 31/661* (2013.01); *A61K 36/064* (2013.01); *A61K 36/38* (2013.01); *A61K 36/45* (2013.01); *A61K 36/899* (2013.01)

(58) Field of Classification Search
None
See application file for complete search history.

(56) References Cited

U.S. PATENT DOCUMENTS

| | | | | |
|---|---|---|---|---|
| 4,794,014 | A * | 12/1988 | Siren | 426/547 |
| 7,427,671 | B1 * | 9/2008 | Matsui et al. | 530/395 |
| 2002/0193302 | A1 | 12/2002 | Ezban et al. | |
| 2003/0039668 | A1 * | 2/2003 | Gulla | A61K 8/553 424/401 |
| 2003/0091651 | A1 | 5/2003 | Xu | |
| 2003/0138393 | A1 | 7/2003 | Pageon | |
| 2004/0063205 | A1 | 4/2004 | Xu | |
| 2004/0191205 | A1 * | 9/2004 | Evans | A61K 8/345 424/70.21 |
| 2005/0239708 | A1 | 10/2005 | Ezban et al. | |
| 2006/0051864 | A1 | 3/2006 | Xu | |
| 2006/0088643 | A1 * | 4/2006 | Fugal | A23L 2/02 426/599 |
| 2006/0275512 | A1 | 12/2006 | Sanberg et al. | |
| 2006/0292692 | A1 | 12/2006 | Xu | |
| 2007/0178527 | A1 * | 8/2007 | Williams et al. | 435/7.1 |
| 2008/0206175 | A1 | 8/2008 | Chung | |
| 2009/0036378 | A1 | 2/2009 | Ezban et al. | |
| 2010/0261276 | A1 | 10/2010 | Park et al. | |
| 2012/0015063 | A1 | 1/2012 | Higuchi et al. | |

FOREIGN PATENT DOCUMENTS

| | | |
|---|---|---|
| CN | 1304305 A | 7/2001 |
| CN | 1205880 C | 6/2005 |
| CN | 1667119 A | 9/2005 |
| CN | 1679818 A | 10/2005 |
| CN | 1955280 A | 5/2007 |
| CN | 101102746 A | 1/2008 |
| CN | 101755046 A | 6/2010 |
| CN | 101965178 A | 2/2011 |
| CN | 101984051 A | 3/2011 |
| EP | 0659349 A1 | 6/1995 |
| EP | 0728468 A2 | 8/1996 |
| JP | 2003-525028 A | 8/2003 |
| JP | 2004-505007 A | 2/2004 |
| JP | 2005-508976 A | 4/2005 |
| JP | 2006-249051 A | 9/2006 |
| JP | 2009-155227 A | 7/2009 |
| KR | 20090092235 A | 8/2009 |
| TW | 201102079 A1 | 1/2011 |
| WO | WO 03/006039 A1 | 1/2003 |

(Continued)

OTHER PUBLICATIONS 2012 http://www.tandurust.com/alternativetherapies/rice-bran-oil-benefits-skin.html.*
Database WPI, Thomson Scientific, London, GB; AN 2009-L62992, XP002720253, abstract of JP 2009-155227 cited Mar. 18, 2013).
Andrae et al., "Role of platelet-derived growth factors in physiology and medicine," Genes & Development, May 15, 2008, 22(10):1276-1312.
Chase et al., "A novel serum-free medium for the expansion of human mesenchymal stem cells," Stem Cell Research & Therapy, Apr. 2, 2010, 1(1):8, 11 pages.
Di Ianni et al., "Mesenchymal cells recruit and regulate T regulatory cells," Experimental Hematology, Feb. 13, 2008, 36(3):309-318.
Nombela-Arrieta et al., "The elusive nature and function of mesenchymal stem cells," Nature Reviews Molecular Cell Biology, Feb. 1, 2011, 12(2):126-131.

(Continued)

*Primary Examiner* — Terry A McKelvey
*Assistant Examiner* — Catheryne Chen
(74) *Attorney, Agent, or Firm* — Foley & Lardner LLP

(57) ABSTRACT

An agent comprising one or more components selected from among cowberry derivatives, mangosteen derivatives, *scutellaria* root derivatives, inositol and inositol phosphate, as an active ingredient, is a novel agent that can effectively promote production of platelet-derived growth factor-BB (PDGF-BB), which contributes to production of mesenchymal stem cells and stabilization of stem cells.

22 Claims, No Drawings
Specification includes a Sequence Listing.

(56) References Cited

FOREIGN PATENT DOCUMENTS

| WO | WO 03/037360 A1 | 5/2003 |
|---|---|---|
| WO | WO 2005/092285 A1 | 10/2005 |

OTHER PUBLICATIONS

Raboy, Victor, "myo-Inositol-1,2,3,4,5,6-hexakisphosphate," Phytochemistry, Nov. 1, 2003, 64(6):1033-1043.

Rodrigues et al., "Growth factor regulation of proliferation and survival of multipotential stromal cells," Stem Cell Research & Therapy, Jan. 1, 2010, 1:32, 13 pages.

Wagner et al., "Mitogenic Signaling via Platelet-Derived Growth Factor β in Metanephric Mesenchymal Cells," Journal of the American Society of Nephrology, Oct. 17, 2007, 18(11):2903-2911.

Caplan et al., "Mesenchymal stem cells as trophic mediators," J. Cell. Biochem., Aug. 1, 2006, 98(5):1075-1084, abstract only.

Cotsarelis et al., "Existence of Slow-Cycling Limbal Epithelial Basal Cells That Can Be Preferentially Stimulated to Proliferate: Implications on Epithelial Stems Cells," Cell, Apr. 21, 1989, 57:201-209.

Dai et al.,, "Allogeneic Mesenchymal Stem Cell Transplantation in Postinfarcted Rat Myocardium: Short- and Long-Term Effects," Circulation, 2005, 112:214-223.

Dalla-Favera et al.,, "A human onc gene homologous to the transforming gene (v-sis) of simian sarcoma virus," Nature, Jul. 2, 1981, 292:31-35.

Da Silva Meirelles et al., "In Search of the In Vivo Identity of Messenchymal Stem Cells," Stem Cells, 2008, 26:2287-2299.

Da Silva Meirelles et al., "Mesenchymal stem cells reside in virtually all post-natal organs and tissues," Journal of Cell Science, 2006, 119:2204-2213.

Fang et al., "Systemic infusion of FLK1(+) mesenchymal stem cells ameliorate carbon tetrachloride-induced liver fibrosis in mice," Transplantation, Jul. 15, 2004, 78(1):83-88.

Fazel et al., "Cell transplantation preserves cardiac function after infarction by infarct stabilization: augmentation by stem cell factor," J. Thorac. Cardiovasc. Surg., Nov. 2005, 130(5):1310, EPub Oct. 13, 2004, abstract only.

Flynn et al., "Review: UC Blood-derived mesenchymal stromal cells: an overview," Cytotherapy, 2007, 9(8):717-726.

Gnecchi et al., "Paracrine action accounts for marked protection of ischemic heart by Akt-modified mesenchymal stem cells," Nature Medicine, Apr. 2005, 11(4):367-368.

Hotamisligil, Gokhan S., "Inflammation and metabolic disorders," Nature, Dec. 14, 2006, 444:860-867.

Igura et al., "Isolation and characterization of mesenchymal progenitor cells from chorionic villi of human placenta," Cytotherapy, 2004, 6(6):543-553.

Kinnaird et al., "Marrow-Derived Stromal Cells Express Genes Encoding a Broad Spectrum of Arteriogenic Cytokines and Promote In Vitro and In Vivo Arteriogenesis Through Paracrine Mechanisms," Circulation Research, 2004, 94:678-685.

Kinnaird et al., "Local Delivery of Marrow-Derived Stromal Cells Augments Collateral Perfusion Through Paracrine Mechanisms," Circulation, 2004, 109:1543-1549.

Le Blanc et al., "Immunomodulation by mesenchymal stem cells and clinical experience," Journal of Internal Medicine, 2007, 262:509-525.

Medzhitov, Ruslan, "Original and physiological roles of inflammation," Nature, Jul. 24, 2008, 454:428-435.

Nishimura et al., "Dominant role of the niche in melanocyte stem-cell fate determination," Nature, Apr. 25, 2002, 416:854-860.

Noiseux et al., "Mesenchymal stem cells overexpressing Akt dramatically repair infracted myocardium and improve cardiac function despite infrequent cellular fusion or differentiation," Mol. Ther., Dec. 2006, 14(6):840-850.

Ortiz et al., "Mesenchymal stem cell engraftment in lung is enhanced in response to bleomycin exposure and ameliorates its fibrotic effects," PNAS, Jul. 8, 2003, 100(14):8407-8411.

Ogawa, Y., "Chromic inflammation: Pathology underlying diseases such as lifestyle related diseases and cancer," Jikken Igaku, 2010, 28:1680-1687, with English translation, 9 pages.

Park et al., "Before They Were Fat: Adipocyte Progenitors," Cell Metabolism, Dec. 3, 2008, 8:454-457.

Pittenger et al., "Multilineage Potntial of Adult Human Mesenchymal Stem Cells," Science, Apr. 2, 1999, 284:143-147.

Suganami et al.,"Metabolic syndrome and 'homeostatic inflammation'," Jikken Igaku, 2010, 28:1717-1723, with English translation, 7 pages.

Tang et al., "Paracrine action enhances the effects of autologous mesenchymal stem cell transplantation on vascular regeneration in rat model of myocardial infarction," Ann. Thorac. Surg., Jul. 2005, 80(1):229-236.

Uccelli et al., "Mesenchymal stem cells: a new strategy for immunosuppression?", Trends Immunol., May 2007, 28(5):219-226.

Watt, Fiona M., "The stem cell compartment in human interfollicular epidermis," Journal of Dermatological Science, 2002, 28:173-180.

Wellen et al., "Inflammation, stress, and diabetes," J. Clin. Invest., May 2005, 115(5):1111-1119.

Wong et al,. "Neural crest-derived cells with stem cell features can be traced back to multiple lineages in the adult skin," JCB, 2006, 175(6):1005-1015.

Zhang et al., "SDF-1 expression by mesenchymal stem cells results in trophic support of cardiac myocytes after myocardial infarction," The FASEB Journal, 2007, 21:3197-3207.

Zhao et al., "Human bone marrow stem cells exhibit neural phenotypes and ameliorate neurological deficits after grafting into the ischemic brain of rats," Exp. Neurol., Mar. 2002, 174(1):11-20.

Huang et al., "Regulation of stromal proliferation, growth arrest, differentiation and apoptosis in benign prostatic hyperplasia by TGF-β," Frontiers in Bioscience 8, Sep. 1, 2003, s740-s749.

Colodny et al., "Inositol—Clinical Applications for Exogenous Use," Alternative Medicine Review, 1998, 3(6):432-447.

Grases et al., "Absorption of myo-inositol hexakisphosphate ($InsP_6$) through the skin: Study of the matrix effects, mechanism of phytate topical absorption," Frontiers in Bioscience, Jan. 1, 2005, 10:799-802.

Udani et al., "Evaluation of Mangosteen juice blend on biomarkers of inflammation in obese subjects: a pilot, dose finding study," Nutrition Journal, 2009, 8:48, 1-7.

Yves Rocher Vegetal Inositol Optimizing Moisturizer, Skin Care Junky, Feb. 4, 2009, http://skincarejunky.blogspot.fr/2090/02/yves-rocher-vegetal-inositol-optimizing.html) retrieved on Feb. 23, 2014.

\* cited by examiner

PLATELET-DERIVED GROWTH FACTOR-BB PRODUCTION PROMOTOR, AND MESENCHYMAL STEM CELL PRODUCTION ACCELERATOR, STEM CELL STABILIZER AND DERMAL REGENERATOR COMPRISING THE SAME

CROSS-REFERENCE TO RELATED APPLICATIONS

This application is a National Stage application of PCT/JP2011/065207, filed Jul. 1, 2011.

TECHNICAL FIELD

The present invention relates to a platelet-derived growth factor-BB (PDGF-BB) production promoter, and to a mesenchymal stem cell production accelerator, a stem cell stabilizer and a dermal regenerator comprising the PDGF-BB production promoter.

BACKGROUND ART

Stem cells are cells having both the property of pluripotency, whereby cells differentiated into different cells are produced, and self-replication, whereby identical cells are produced by cell division. Stem cells derived from the embryo at the early stages of development of the fertilized ovum are known as embryonic stem cells (ES cells). Human ES cells hold promise for use in regenerative medicine, but ethical problems involved in the use of fertilized eggs has prevented the creation of new human ES cells.

Recently, induced pluripotent stem cells (iPS cells) have also been the focus of attention, as cells having properties similar to ES cells. However, numerous problems including cell canceration and creation efficiency have been encountered in the creation of iPS cells. On the other hand, somatic stem cells, which have the ability to differentiate into specific tissues, are obtained from the patient's own body tissues such as bone marrow, for example, and therefore do not involve the ethical problems associated with embryonic stem cells.

Epidermal stem cells (Non-patent document 1) are well known to be present in the basal epidermal layer of skin, and follicular epithelial stem cells (Non-patent document 2) or melanocyte stem cells (Non-patent document 3) have been reported in a region known as the follicular bulge region. On the other hand, fibroblasts having elongated spindle shapes are present in fiber components in the dermis that are composed mainly of collagen, but it has not yet been determined whether or not stem cells are present in dermal fibroblasts. Also, while it is known that skin-derived precursors (SKP) that differentiate into multiple cell lines such as fat, glia, cartilage and muscle are present in the skin (Non-patent document 4), the relationship between dermal fibroblasts and SKP has not been elucidated.

Mesenchymal stem cells that have separated from the bone marrow as fibroblast precursors (Non-patent document 5) differentiate into a variety of cells of the mesenchyme (bone cells, muscle cells, chondrocytes, tendon cells, adipocytes and the like), and therefore their application in regenerative medicine for reconstruction of bone, blood vessels and muscle is promising. Recently it has been suggested that they may be abundantly present in tissue that contains mesenchymal tissue, and mesenchymal stem cells have been isolated from fat, umbilical cord and placenta as well (Non-patent documents 6-8).

Recent findings have shown that mesenchymal stem cells are present in systemic blood vessels as pericytes and function to maintain vascular stabilization and tissue homeostasis (Non-patent documents 9 and 10).

When blood vessels are destroyed at sites of tissue damage or its periphery, the mesenchymal stem cells, or pericytes, separate from the blood vessels and proliferate to supply the lost cells (Non-patent documents 11-14) while releasing bioactive factors to protect tissue (Non-patent documents 15-19) and functioning to repair and regenerate the damaged tissue. It has been reported that these secreted factors function not only for angiogenesis and anti-apoptosis, but also to powerfully inhibit immunity (Non-patent documents 21 and 22), and to suppress destruction of tissue damaged by T cells or B cells (Non-patent documents 9 and 22).

In addition, mesenchymal stem cells are known to exhibit antifibrinolytic action (Non-patent documents 23 and 24) and effects against multiple sclerosis and diabetes (Non-patent document 9).

On the other hand, it is becoming clear that chronic inflammation is a fundamental pathology common to a variety of conditions (for example, metabolic syndrome, arteriosclerotic disease, cancer, neurodegenerative disease and autoimmune disease) (Non-patent document 25). For example, it has been reported that endothelial cell dysfunction and insulin resistance are induced by chronic inflammation, leading to various diseases such as diabetes or arteriosclerotic disease (Non-patent document 26). Furthermore, it has been found that obese adipose tissue itself leads to inflammatory changes (Non-patent documents 27-29). The fact that chronic inflammation occurs in the vicinity of blood vessels suggests that chronic inflammation also involves a failure of interaction between mesenchymal stem cells, which are pericytes, and blood vessels.

Based on this knowledge, it is believed that promoting the production of, and stabilizing, mesenchymal stem cells, would be highly effective for a variety of purposes, including vascular stabilization, maintaining tissue homeostasis, repair and regeneration of damaged tissue, preventing fibrosis, preventing and treating diseases such as multiple sclerosis and diabetes and preventing and ameliorating conditions associated with chronic inflammation, such as metabolic syndrome.

The present inventors have already reported that mesenchymal stem cells are present in the dermis as well, and have established a method for efficiently isolating mesenchymal stem cells from the dermis (Japanese Patent Application No. 2009-213291). Considering the function of mesenchymal stem cells described above, it is believed that stabilizing and promoting the production of mesenchymal stem cells in the dermis is also effective for improving the condition of and regenerating the dermis.

In addition, the present inventors have elucidated in greater detail the locations in which mesenchymal stem cells are present in the dermis and subcutaneous fat, and have found that platelet-derived growth factor-BB (PDGF-BB) is involved in the localization of mesenchymal stem cells, while also determining that promoting production of PDGF-BB in vascular endothelial cells contributes to increased production of and stabilization of mesenchymal stem cells (Japanese Patent Application No. 2010-209705).

Platelet-derived growth factor (PDGF) is a growth factor involved in regulation of migration and proliferation of mesenchymal stem cells including fibroblasts, smooth muscle cells and glia cells, and it is produced by a variety of cells such as epithelial cells and endothelial cells. At least 4 types of PDGF exist, PDGF-A, B, C and D, the A chain and B chain adopting homo or hetero dimer structures through formation of disulfide bonds, to produce the 3 isoforms (PDGF-AA, AB, BB). PDGF is known to exhibit its physiological action through PDGF receptor (PDGFR), a tyrosine kinase receptor. The gene for PDGF-B is known and has been genetically cloned (Non-patent document 30).

Discovering a component effective for promoting production of PDGF-BB is expected to be useful to promote production of mesenchymal stem cells and stabilize stem cells, and to thus be effective for a variety of purposes as described above.

CITATION LIST

Non-Patent Literature

[Non-patent document 1] Watt F M, J Dermatol Sci, 28:173-180, 2002
[Non-patent document 2] Cotsarelis G et al., Cell, 57:201-209, 1989
[Non-patent document 3] Nishimura E K et al., Nature, 416:854-860, 2002
[Non-patent document 4] Wong C E al., J Cell Biol, 175:1005-1015, 2006
[Non-patent document 5] Pittenger M F et al., Science, 284:143-147, 1999
[Non-patent document 6] Park K W et al., Cell Metab, 8:454-457, 2008
[Non-patent document 7] Flynn A et al., Cytotherapy, 9:717-726, 2007
[Non-patent document 8] Igura K et al., Cytotherapy, 6:543-553, 2004
[Non-patent document 9] da Silva Meirelles L et al., Stem Cells, 2008 September; 26(9):2287-2299
[Non-patent document 10] da Silva Meirelles L et al., J Cell Sci, 2006; 119:2204-2213
[Non-patent document 11] Dai W D et al., Circulation, 2005; 112:214-223
[Non-patent document 12] Fazel S et al., J Thorac Cardiovasc Surg, 2005; 130:1310-1318
[Non-patent document 13] Noiseux N et al., Mol Ther, 2006; 14:840-850
[Non-patent document 14] Zhao L R et al., Exp Neurol, 2002; 174:11-20
[Non-patent document 15] Gnecchi M et al., Nat Med, 2005; 11:367-368
[Non-patent document 16] Kinnaird T et al., Circ Res, 2004; 94:678-685
[Non-patent document 17] Kinnaird T et al., Circulation, 2004; 109:1543-1549
[Non-patent document 18] Tang Y L et al., Ann Thorac Surg, 2005; 80:229-237
[Non-patent document 19] Zhang M et al., FASEB J, 2007; 21:3197-3207
[Non-patent document 20] Le Blanc K et al., J Intern Med, 2007; 262:509-525
[Non-patent document 21] Uccelli A et al., Trends Immunol, 2007; 28:219-226
[Non-patent document 22] Caplan A I et al., J Cell Biochem, 2006; 98:1076-1084
[Non-patent document 23] Fang B J et al., Transplantation, 2004; 78:83-88
[Non-patent document 24] Ortiz L A et al., Proc Natl Acad Sci USA, 2003; 100:8407-841
[Non-patent document 25] Ogawa, Y., Jikken Igaku, 28:1680-1687, 2010
[Non-patent document 26] Medzhitov R, Nature, 454:428-35, 2008
[Non-patent document 27] Hotamisligil G S, Nature, 444 (7121):860-7, 2006
[Non-patent document 28] Wellen K E et al., J Clin Invest, 115(5):1111-9, 2005
[Non-patent document 29] Sugami, T et al., Jikken Igaku, 28:1717-1723, 2010
[Non-patent document 30] Dalla-Favera R et al., Nature, 292:31-35, 1981

DISCLOSURE OF THE INVENTION

Problems to be Solved by the Invention

The present invention has been accomplished in light of the background described above, and its object is to provide an agent effective for promoting production of PDGF-BB, as well as to provide an agent effective for promoting production of and/or stabilizing mesenchymal stem cells using the same.

Means for Solving the Problems

The present inventors have conducted much research on a large variety of materials and, as a result of screening for drugs that promote production of PDGF-BB, have completed this invention upon finding that the plant derivatives cowberry, mangosteen and *scutellaria* root, as well as inositol and inositol phosphate, all exhibit notable effects of promoting production of PDGF-BB.

The present application thus encompasses the following inventions.

[1] A platelet-derived growth factor-BB (PDGF-BB) production promoter comprising one or more components selected from among cowberry derivatives, mangosteen derivatives, *scutellaria* root derivatives, inositol and inositol phosphate, as an active ingredient.

[2] A PDGF-BB production promoter according to [1], which comprises inositol and further comprises a yeast extract.

[3] A PDGF-BB production promoter according to [1] or [2], wherein the inositol is inositol phosphate derived from rice bran.

[4] A mesenchymal stem cell production accelerator comprising a PDGF-BB production promoter according to any one of [1] to [3].

[5] A stem cell stabilizer comprising a PDGF-BB production promoter according to any one of [1] to [3].

[6] A dermal regenerator comprising a PDGF-BB production promoter according to any one of [1] to [3].

Effect of the Invention

According to the invention there is provided an agent effective for promoting production of PDGF-BB, as well as an agent effective for promoting production of and stabilizing mesenchymal stem cells, that employs the aforementioned agent.

BEST MODE FOR CARRYING OUT THE INVENTION

[Cowberry Derivative]

Cowberry (scientific name: *Vaccinium vitis-idaea* L.) is a plant of the family Ericaceae, genus *Vaccinium*. According to the invention, cowberry derivatives may be cowberry flowers, flowering spikes, capsules, peels, fruit, stems, leaves, branches, side leaves, stalks, bark, rhizomes, root bark, roots, seeds or the entire plant, that has been pulverized and squeezed, or extracted with a solvent after pulverizing, or decomposed after pulverizing, by treatment such as enzyme treatment or mechanical processing.

The extraction solvent used as the extraction solvent for extraction of cowberry may be any desired one, and for example, water or organic solvents including alcohols such as methanol, ethanol, propylene glycol, 1,3-butylene glycol or glycerin, water-containing alcohols, chloroform, dichloroethane, carbon tetrachloride, acetone, ethyl acetate and the like may be used either alone or in combinations.

The extraction may be carried out at ordinary temperature, or it may be carried out with heating (for example, using a heated solvent such as warm water or hot water).

The extract obtained by extraction with the solvent may be used directly, or the concentrated extract may be used, or the extract may be depleted of impurities by an adsorption process using an ion exchange resin or the like, or it may be subjected to adsorption on a porous polymer (for example, AMBERLITE XAD-2) column and then eluted with methanol or ethanol and concentrated. An extract obtained by a known partition method (a partition method using water/ethyl acetate, for example) may also be used.

When the cowberry is to be decomposed, "single-cell preparation" may be carried out, in which the intercellular substances are selectively decomposed to maintain the cellular forms. Reference may be made to the method described in Japanese Unexamined Patent Publication No. 2002-193734, for example. Specifically, this is treatment in which the plant is subjected to enzymolysis, mechanical decomposition or the like for selective decomposition or disruption of the intercellular substances with virtually no decomposition of the cell walls, for resolution of the substance into cellular units having the cellular forms maintained, and obtaining a paste-like form, liquid composition or freeze-dried product. Enzyme treatment may be used to accomplish such selective decomposition. For example, products that have been isolated or isolated and purified by commonly known methods from enzyme materials such as *Rhizopus* or *Aspergillus* may be used, or commercial products may be used. When these single-cell preparation enzymes are to be used for cowberry, they are preferably allowed to act under optimal conditions such as the optimum temperature and optimum pH of the enzyme, in the minimal necessary amounts. The optimum temperature for a single-cell preparation enzyme is 30-45° C., and the optimum pH is 4-6. The portion remaining after enzyme reaction may be removed using an approximately 20 mesh sieve to obtain a cowberry derivative that can be added to a composition for external use.

Also, in addition to the suspension of the single-cell preparation, the suspension may be prepared as a monocellular paste, or its dried form, obtained by dehydration by a method such as centrifugal separation, for use according to the invention.

Cowberry has been used in the past as an external preparation comprising a single-cell cowberry preparation (Japanese Unexamined Patent Publication No. 2002-193734), as a bactericidal, antibacterial or anti-dandruff cosmetic (Japanese Unexamined Patent Publication SHO No. 61-238719), as an elastase activity inhibitor (Japanese Unexamined Patent Publication No. 2002-363088), as an active enzyme remover (Japanese Unexamined Patent Publication No. 2002-363027), as a melanin production inhibitor (Japanese Unexamined Patent Publication No. 2002-363057), as a lipid peroxide production inhibitor (Japanese Unexamined Patent Publication No. 2002-363089), as a collagenase activity inhibitor (Japanese Unexamined Patent Publication No. 2003-12531), as a hyaluronidase activity inhibitor (Japanese Unexamined Patent Publication No. 2003-73287), as a metalloprotease expression inhibitor (Japanese Unexamined Patent Publication No. 2002-193738), as a glycation inhibitor (Japanese Patent Public Inspection No. 2004-505007) and as a skin-damage control agent against skin disorders such as pachyderma and scleroderma (Japanese Unexamined Patent Publication No. 2005-306850); however, it has been completely unknown to date that cowberry derivatives have PDGF-BB production-promoting effects, mesenchymal stem cell production-promoting effects, stem cell stabilizing effects and dermis stabilizing effects, and these effects have been discovered for the first time by the present inventors.

[Mangosteen Derivatives]

Mangosteen (scientific name: *Garcinia mangostana*) is a plant of the family Otogiriso, genus *Garcinia*. According to the invention, a mangosteen derivative may be a capsule, peel, fruit, stem, leaf, branch, side leaf, stalk, bark, rhizome, root bark, root, seed or entire plant of mangosteen, that has been pulverized and squeezed, or extracted with a solvent after pulverizing.

When mangosteen is to be extracted, any solvent allowing extraction may be used as the extraction solvent, and for example, extraction may be performed using any of various organic solvents including lower alcohols such as methanol, ethanol, propyl alcohol, isopropyl alcohol, butanol or isobutanol, or aqueous lower alcohols, polyhydric alcohols such as propylene glycol or 1,3-butylene glycol or aqueous polyhydric alcohols, acetone, ethyl acetate ester or the like, with the solvent subsequently distilled off.

The extraction may be carried out at ordinary temperature, or it may be carried out with heating (for example, using a heated solvent such as warm water or hot water).

An enzyme may also be added to the solvent for the extraction treatment. Addition of an enzyme can disintegrate the cellular tissue of fruit and further increase the extraction efficiency. The enzyme used is preferably a cellular tissue-degrading enzyme. Examples of such enzymes include pectinases, cellulases, hemicellulases, α-amylases and phytases. Any of these enzymes may be used alone, or two or more thereof may be used in combination.

The extract obtained using the extraction solvent may be used directly, or the extraction solvent may be distilled off and the extract used after drying as necessary.

Mangosteen has been used in the past as an ultraviolet absorber (Japanese Unexamined Patent Publication HEI No. 9-87155), as an MMP inhibitor (Japanese Unexamined Patent Publication No. 2003-252745) and as a fibroblast activator (Japanese Unexamined Patent Publication No. 2006-249051), and it has been known to have effects on xanthone derivative production and collagen production (Japanese Unexamined Patent Publication No. 2009-84169); however, it has been completely unknown to date that mangosteen derivatives have PDGF-BB production-promoting effects, mesenchymal stem cell production-promoting effects, stem cell stabilizing effects and dermis stabilizing effects, and these effects have been discovered for the first time by the present inventors.

[*Scutellaria* Root Derivatives]

*Scutellaria* root (scientific name: *Scutellaria baicalensis* Georgi, Labiatae) is a plant of the family Lamiaceae, genus *Scutellaria*. According to the invention, a *scutellaria* root derivative may be a capsule, peel, fruit, stem, leaf, branch, side leaf, stalk, bark, rhizome, root bark, root, seed or entire plant of *scutellaria* root, that has been pulverized and squeezed, or extracted with a solvent after pulverizing.

For extraction of *scutellaria* root, the extraction solvent may be any desired solvent that is commonly used for plant extraction, and examples include water, lower alcohols such as methanol, ethanol, isopropanol and n-butanol, polyhydric alcohols such as propylene glycol and 1,3-butylene glycol, or hydrous forms of these alcohols, and hydrocarbon-based solvents such as n-hexane and toluene. These may be used alone, or any two or more thereof may be used in combination. Lower alcohols such as methanol or ethanol are preferably used.

The extraction may be carried out at ordinary temperature, or it may be carried out with heating (for example, using a heated solvent such as warm water or hot water).

An enzyme may also be added to the solvent for the extraction treatment. Addition of an enzyme can disintegrate the cellular tissue of fruit and further increase the extraction efficiency. The enzyme used is preferably a cellular tissue-degrading enzyme. Examples of such enzymes include pectinases, cellulases, hemicellulases, α-amylases and phytases. Any of these enzymes may be used alone, or two or more thereof may be used in combination.

The extract obtained using the extraction solvent may be used directly, or the extraction solvent may be distilled off and the extract used after drying as necessary.

*Scutellaria* root has been used in the past as a hair papilla activating agent (Japanese Unexamined Patent Publication HEI No. 11-240823), as a hyaluronic acid production enhancer (Japanese Unexamined Patent Publication HEI No. 10-95735), as an immunostimulant to prevent ultraviolet-induced loss of skin immunological function (Japanese Unexamined Patent Publication HEI No. 11-71295), as an anti-inflammatory drug (Japanese Unexamined Patent Publication No. 2006-8536) and as an antioxidant (Japanese Unexamined Patent Publication HEI No. 5-238925); however, it has been completely unknown to date that *scutellaria* root derivatives have PDGF-BB production-promoting effects, mesenchymal stem cell production-promoting effects, stem cell stabilizing effects and dermis stabilizing effects, and these effects have been discovered for the first time by the present inventors.

[Inositol/Inositol Phosphate]

Inositol is considered to be a form of vitamin B, and it is also known to be biosynthesized from glucose in the body. Inositol is found in plants such as cereals, sugar, beans and fruits. Inositol is often present in a form with phosphorylated hydroxy groups (inositol phosphate). According to the invention, inositol phosphate may also be used. Various stereoisomers of inositol are also included in the inositol used for the invention. Stereoisomers of inositol include cis-inositol (1,2,3,4,5,6/0-inositol), epi-inositol (1,2,3,4,5/6-inositol), allo-inositol (1,2,3,4/5,6-inositol), myo-inositol 1,2,3,5/4,6-inositol, muco-inositol (1,2,4,5/3,6-inositol), neo-inositol (1,2,3/4,5,6-inositol), chiro-inositol (1,2,4/3,5, 6-inositol) and scyllo-inositol (1,3,5/2,4,6-inositol). Inositol phosphate may a compound having any one or more of the 6 hydroxy groups of inositol phosphorylated. Preferred is phytic acid, which is a compound having all 6 of the hydroxy groups of inositol phosphorylated. The inositol or inositol phosphate used for the invention is preferably derived from rice bran. Any salts of inositol phosphate may also be used for the invention.

According to an embodiment of the invention, the inositol and inositol phosphate may be used as appropriate dilutions obtained by dissolution of simple powder in a medium.

The inositol and inositol phosphate may also be combined with other substances to improve the PDGF-BB production-promoting effect. Such other substances may be yeast extracts, such as Biodyne® EMPP (product of Arch Personal Care Products L.P.). When such an extract is to be used, the extract may be added to medium at about 0.1%, in terms of concentration from the dry residue of the extract.

Inositol and inositol phosphate have been used in the past as inositol-containing cosmetic compositions for aged skin and/or for stress-ravaged skin (Japanese Patent Public Inspection No. 204-501069), as cosmetic compositions containing inositol phosphate (especially phytic acid and its salts) to reduce or prevent signs of lipedema (Japanese Unexamined Patent Publication HEI No. 8-253406), and as compositions for skin moisture retention and/or skin protection and/or skin aging prevention (Japanese Unexamined Patent Publication No. 2010-150258). Examples as B vitamins include cell-activating external preparations for skin containing vitamin B2 and B6 (Japanese Unexamined Patent Publication HEI No. 9-241146) and vitamin B-containing antioxidants (Japanese Unexamined Patent Publication HEI No. 7-277939 and Japanese Unexamined Patent Publication No. 205306831). However, it has been completely unknown that B vitamins and inositol or inositol phosphate have PDGF-BB production-promoting effects, mesenchymal stem cell production-promoting effects, stem cell stabilizing effects and dermis stabilizing effects, and this has been discovered for the first time by the present inventors.

[PDGF-BB Production Promoter, Mesenchymal Stem Cell Production Accelerator, Stem Cell Stabilizer and Dermal Regenerator]

The PDGF-BB production promoter of the invention comprises one or more components selected from among cowberry derivatives, mangosteen derivatives, *scutellaria* root derivatives, inositol and inositol phosphate, as an active ingredient. The mesenchymal stem cell production accelerator, stem cell stabilizer and dermal regenerator of the invention comprise a PDGF-BB production promoter of the invention that includes an active ingredient as described above. The PDGF-BB production promoter, mesenchymal stem cell production accelerator, stem cell stabilizer and dermal regenerator of the invention (hereunder these will also be collectively referred to as "agents of the invention") may contain any of the aforementioned active ingredients alone, or two or more thereof in any desired combination and proportion.

Based on knowledge of the present inventors, as mentioned above, PDGF-BB contributes to localization of mesenchymal stem cells, and promotes production of PDGF-BB by vascular endothelial cells, thereby helping to promote production of and stabilize mesenchymal stem cells (Japanese Patent Application No. 2010-209705). That is, the PDGF-BB production promoter of the invention can be very effectively used to promote production of and stabilize mesenchymal stem cells.

Also, as mentioned above, it is known that promoting the production of, and stabilizing, mesenchymal stem cells, is highly effective for vascular stabilization, maintaining tissue homeostasis, repair and regeneration of damaged tissue (especially dermal regeneration), preventing fibrosis, preventing and treating diseases such as multiple sclerosis and diabetes and preventing and ameliorating conditions associated with chronic inflammation, such as metabolic syndrome. Thus, a mesenchymal stem cell production accelerator and stem cell stabilizer of the invention employing the PDGF-BB production promoter of the invention can be very effectively used for such purposes.

The agents of the invention may be prepared as compositions comprising the aforementioned active ingredient in combination with one or more other components, such as excipients, carriers and/or diluents. The constitution and form of the composition may be as desired, and it may be appropriately selected depending on conditions including the active ingredient and the purpose of use. The composition may be prepared by a common method as a formulation in an appropriate combination with an excipient, carrier and/or diluent or other components, depending on the dosage form.

The agents of the invention may be mixed with various foods and beverages or feeds (pet food or the like) for ingestion by a human or animal. They may also be combined in cosmetics or the like for humans or animals, or administered as medical preparations to humans or animals.

Specifically, when an agent of the invention is to be added to a food or beverage or feed, the content (dry weight) of the plant body or its extract may be appropriately determined according to the type of plant, the purpose, the form and the method of use. For example, the content may be such that the consumption of a plant or its extract per day for adults is 0.5 mg-1 g (dry residue) for Indian gooseberry extract or about 0.5 mg-3 g for lingonberry extract. In particular, when it is to be used as a health food or beverage, it is preferably added to 10 mg-500 mg (dry residue) for Indian gooseberry extract or 10 mg-1.5 g (dry residue) for lingonberry extract, per day for adults, so that the desired effect of the active ingredient of the invention is adequately exhibited.

The form of the food or beverage or feed may be any desired form, and for example, it may be molded into granular, particulate, paste-like, gel-like, solid or liquid form. These forms may be approximately combined with various known substances approved for addition to foods and beverages, including excipients such as binders, disintegrators, thickeners, dispersing agents, reabsorption accelerators, taste correctives, buffering agents, surfactants, dissolving aids, preservatives, emulsifiers, isotonizing agents, stabilizers and pH regulators.

When an agent of the invention is to be added to a cosmetic, the content (dry weight) of the plant body or its extract may be appropriately determined according to the type of plant, the purpose, the form and the method of use. For example, Indian gooseberry extract or lingonberry extract may be added at 0.00001%-50% (based on dry weight), and more preferably 0.0001%-5% (based on dry weight), of the total cosmetic.

In addition to the aforementioned components, there may also be appropriately added, as necessary, components that are commonly used in external preparations for skin such as cosmetics or pharmaceuticals, including antioxidants, oils, ultraviolet protecting agents, surfactants, thickeners, alcohols, powder constituents, coloring materials, aqueous components, water and skin nutrient preparations, in ranges that do not interfere with the effect of the invention.

In addition, there may also be added appropriate amounts of metal ion chelators such as disodium edetate, trisodium edetate, sodium citrate, sodium polyphosphate, sodium metaphosphate and gluconic acid, antiseptic agents such as methylparaben, ethylparaben and butylparaben, drugs including caffeine, tannin, verapamil, tranexamic acid and its derivatives, licorice extract, glabridin, Chinese quince fruit hot water extract, galenicals, tocopherol acetate, glycyrrhizic acid and its derivatives and salts, skin whiteners such as vitamin C, magnesium ascorbate phosphate, glucoside ascorbate, arbutin and kojic acid, and saccharides such as glucose, fructose, mannose, sucrose and trehalose.

These external preparations for skin may be widely used in cosmetics, quasi drugs and the like that are applied externally to the skin, and most preferably in cosmetics. The dosage form may be any that can be applied to skin, such as a solution, solubilized form, emulsion, powder dispersion, water-oil bilayer, water-oil-powder trilayer, ointment, cosmetic water, gel, aerosol or the like.

When an agent of the invention is to be used as a cosmetic, it is preferably used in the form of a cosmetic water, latex, foundation, lipstick, lip cream, cleansing cream, massage, cream, pack, hand cream, hand powder, body, shampoo, body, lotion, body, cream, bath cosmetic or the like, in which case components normally added and formulated with such forms may be included as appropriate, including components such as humectants, aromatics, solubilizing agents, stabilizers, ultraviolet absorbers, ultraviolet scattering agents and the like.

When an agent of the invention is to be applied as an external preparation, the content (dry weight) of the plant body or its extract may be appropriately determined according to the type of plant, the purpose, the form and the method of use. For example, it is preferably used at 0.00001%-50% (based on dry weight) in a cosmetic, or preferably at 0.0001%-5% (based on dry weight) in a food or beverage.

When an agent of the invention is to be used as a quasi drug, the formulation may be used as appropriate in either peroral or parenteral form (for intravenous administration, intraperitoneal administration or the like). The dosage form may be as desired, and may be appropriately prepared by a known method for any form, including oral solid formulations such as tablets, granules, powder or capsules, oral liquid formulations such as internal liquid drugs or syrups, or parenteral liquid formulations such as injections. Such medical preparations may appropriately contain commonly used excipients such as binders, disintegrators, thickeners, dispersing agents, reabsorption accelerators, taste correctives, buffering agents, surfactants, dissolving aids, preservatives, emulsifiers, isotonizing agents, stabilizers and pH regulators.

An external preparation may be generally applied in a form such as an ointment, and it is preferably used in the form of a lotion, suspending agent, emulsion, liquid drug, ointment or medical patch. Forms that may be applied for the agent of the invention are not limited to these dosage forms.

The expression level of the PDGF-BB gene in mesenchymal stem cells upon administration of an agent of the invention can be determined and evaluated by measuring the level of PDGF-BB, for example. Preferably, the measurement is conducted by a method that is known in the field using antibodies specific for PDGF-BB, and for example, it may be conducted by an immunostaining method using a fluorescent substance, dye, enzyme and the like, or by Western blotting or an immunoassay method such as ELISA or RIA. Also, the total RNA in the mesenchymal stem cells may be extracted, and the amount of mRNA coding for PDGF-B measured for determination and evaluation. Methods of mRNA extraction and measurement are well-known in the field, and for example, RNA is quantitated by quantitative Polymerase Chain Reaction (PCR), such as Real-Time Polymerase Chain Reaction (RT-PCR). Selection of a primer suitable for RT-PCR may be carried out by a method known to those skilled in the art.

EXAMPLES

The present invention will now be explained in greater detail by examples. However, the invention is in no way limited by the examples.

[Evaluation Sample]

The following were used as samples for evaluation of the PDGF-BB production-promoting effect.

Inositol:

Commercially available inositol powder (myo-inositol, product of Wako Pure Chemical Industries, Ltd.) was dissolved in PBS and then used in an amount for 10 ppm in the medium described below.

Phytic Acid:

Commercially available phytic acid (50% aqueous solution, product of Nacalai Tesque, Inc.) was used in an amount for 10 ppm in the medium described below.

Scutellaria Root Extract

Scutellaria roots with the pellicle removed were extracted with 70 vol % ethanol (mixture of water and ethanol in a volume ratio of 3:7) and the extract was used. The extract was dried and stored, and 70 vol % ethanol was added for dissolution immediately before use, in an amount for 15 ppm in the medium described below (based on the dry weight of the extract).

Cowberry CRS (Cell Release System):

The suspension used comprised 1,3-BG added at 40 vol % to a cell suspension obtained by treating cowberry leaves with a cytolytic enzyme (macerozyme A). The suspension was stored as a liquid and used in an amount for 30 ppm in the medium described below (based on the dry weight of the extract).

Mangosteen Bark Extract:

Mangosteen bark was extracted with 70 vol % 1,3-BG (a mixture of water and 1,3-BG in a volume ratio of 3:7) and the obtained extract was used. The extract was dried and stored, and 70 vol % 1,3-BG was added for dissolution immediately before use, in an amount for 10 ppm in the medium described below (based on the dry weight of the extract).

[Evaluation of PDGF-BB Production-Promoting Effect in Vascular Endothelial Cells]

Human vascular endothelial cells HUVEC were subcultured with EGM-2 medium (Sanko Junyaku Co., Ltd.), and cells of the 4th subculture were suspended in VEGF-A-free Humedia-EG2 medium (Kurabo Industries, Ltd.) and seeded in a collagen-coated 24-well multiplate (Asahi Glass Co., Ltd.) at a 20,000 cell ratio, and culturing was conducted in the presence of 5% $CO_2$ for 3-5 days until the cells reached confluence at 37° C. After exchange with Humedia-EG2 medium (Kurabo Industries, Ltd.) containing each sample added to the specified concentration or an added solvent dissolving each evaluation sample, culturing was continued for 2 days. The mRNA was extracted and purified from the cultured cells using an RNA extraction reagent MagNA Pure LC mRNA HS kit (Roche) and an automatic nucleic acid extraction apparatus MagNA Pure LC 1.0 Instrument (Roche), according to the manufacturer's protocol. For each sample, an equal volume of mRNA was used as template for one-step quantitative real time (RT)-PCR of the PDGF-B gene using primer pairs of SEQ ID NO: 1 and 2 listed below, the reaction reagent QuantiFast SYBR Green RT-PCR Kit (Qiagen) and a LightCycler reactor (Roche). The composition conditions were according to the protocol by Qiagen. The RT-PCR conditions were RT reaction at 50° C. for 20 minutes, initial denaturation at 95° C. for 15 minutes, denaturation at 94° C. for 15 seconds, annealing at 60° C. for 20 seconds and extension at 72° C. for 30 seconds. G3PDH was used as an internal standard (primer pair of SEQ ID NO: 3 and 4), and the mRNA level was calibrated with respect to the control.

PDGF-B:

```
Forward primer:
                                      (SEQ ID NO: 1)
5'-CCTGGCATGCAAGTGTGA-3'

Reverse primer:
                                      (SEQ ID NO: 2)
5'-CCAATGGTCACCCGATTT-3'
```

G3PDH:

```
Forward primer:
                                      (SEQ ID NO: 3)
5'-GCACCGTCAAGGCTGAGAAC-3'

Reverse primer:
                                      (SEQ ID NO: 4)
5'-ATGGTGGTGAAGACGCCAGT-3'
```

[Evaluation Results]

The expression levels of PDGF-BB mRNA for each sample are shown in the following table, in comparison to the expression levels for the control (solvent dissolving each evaluation sample), as obtained by the evaluation procedure described above. The following results show that the components have activity of promoting PDGF-BB expression.

TABLE 1

| Drug name | Concentration (ratio to medium) | PDGF-BB expression (vs. control) |
|---|---|---|
| Inositol | 10 ppm | 1.37 |
| Phytic acid | 10 ppm | 1.20 |
| Scutellaria root extract | 15 ppm | 1.56 |
| Cowberry CRS | 30 ppm | 1.85 |
| Mangosteen bark extract | 10 ppm | 1.31 |

[Sequence Listing]

What is claimed is:

1. A method for promoting production of mesenchymal stem cells, comprising administering to a subject in need thereof an effective amount of a composition comprising a PDGF-BB production promoter as an active ingredient, wherein the effective amount is an amount sufficient to promote production of platelet-derived growth factor-BB (PDGF-BB), wherein the PDGF-BB production promoter is inositol or inositol phosphate, as the active ingredient, and wherein production of mesenchymal stem cells is increased.

2. A method for stabilizing stem cells, comprising administering to a subject in need thereof an effective amount of a composition comprising a PDGF-BB production promoter as an active ingredient, wherein the effective amount is an amount sufficient to promote production of platelet-derived growth factor-BB (PDGF-BB), wherein the PDGF-BB production promoter is inositol or inositol phosphate, as the active ingredient, and wherein the subject's stem cells are stabilized.

3. The method according to claim 1, wherein the composition comprising a PDGF-BB production promoter is administered to the skin of the subject.

4. The method according to claim 1, wherein the active ingredient is administered with a yeast extract.

5. The method according to claim 1, wherein the inositol or inositol phosphate is derived from rice bran.

6. The method according to claim 3, wherein the dermis of the subject is regenerated.

7. The method according to claim 1, wherein the effective amount is at least 10 ppm of the composition.

8. The method according to claim 1, wherein the effective amount is at least 15 ppm of the composition.

9. The method according to claim 1, wherein production of PDGF-BB increases at least 1.20-fold.

10. The method according to claim 1, wherein production of PDGF-BB increases at least 1.30-fold.

11. The method according to claim 1, wherein production of PDGF-BB increases at least 1.50-fold.

12. The method according to claim 1, wherein production of PDGF-BB increases at least 1.80-fold.

13. The method according to claim 2, wherein the active ingredient is administered with a yeast extract.

14. The method according to claim 2, wherein the inositol or inositol phosphate is derived from rice bran.

15. The method according to claim 2, wherein the composition comprising a PDGF-BB production promoter is administered to the skin of the subject.

16. The method according to claim 15, wherein the dermis of the subject is regenerated.

17. The method according to claim 2, wherein the effective amount is at least 10 ppm of the composition.

18. The method according to claim 2, wherein the effective amount is at least 15 ppm of the composition.

19. The method according to claim 2, wherein production of PDGF-BB increases at least 1.20-fold.

20. The method according to claim 2, wherein production of PDGF-BB increases at least 1.30-fold.

21. The method according to claim 2, wherein production of PDGF-BB increases at least 1.50-fold.

22. The method according to claim 2, wherein production of PDGF-BB increases at least 1.80-fold.

* * * * *

UNITED STATES PATENT AND TRADEMARK OFFICE
CERTIFICATE OF CORRECTION

| | |
|---|---|
| PATENT NO. | : 10,391,137 B2 |
| APPLICATION NO. | : 13/138417 |
| DATED | : August 27, 2019 |
| INVENTOR(S) | : Soma et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2101 days.

Signed and Sealed this
Fourteenth Day of July, 2020

Andrei Iancu
*Director of the United States Patent and Trademark Office*

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: PDGF-B Forward Primer

<400> SEQUENCE: 1
cctggcatgc aagtgtga

```
<210> SEQ ID NO 2
<211> LENGTH: 18
<212> TYPE: DNA
<213> ORGANISM: Artificial Sequence
<220> FEATURE:
<223> OTHER INFORMATION: PDGF-B Reverse Primer

<400> SEQUENCE: 2
ccaatggtca cccgattt                                          18

<210> SEQ ID NO 3
<211> LENGTH: 20
<212> TYPE: DNA
<213> ORGANISM: Artificial Sequence
<220> FEATURE:
<223> OTHER INFORMATION: G3PDH Forward Primer

<400> SEQUENCE: 3
gcaccgtcaa ggctgagaac                                        20

<210> SEQ ID NO 4
<211> LENGTH: 20
<212> TYPE: DNA
<213> ORGANISM: Artificial Sequence
<220> FEATURE:
<223> OTHER INFORMATION: G3PDH Reverse Primer

<400> SEQUENCE: 4
atggtggtga agacgccagt                                        20
```